United States Patent
Pinnell et al.

(10) Patent No.: US 9,248,082 B2
(45) Date of Patent: Feb. 2, 2016

(54) ANTI-AGING COMPOSITION CONTAINING PHLORETIN

(75) Inventors: Sheldon R. Pinnell, Durham, NC (US); Jan Zielinski, Vista, CA (US); Isabelle Hansenne, Westfield, NJ (US)

(73) Assignee: L'OREAL (FR)

( * ) Notice: Subject to any disclaimer, the term of this patent is extended or adjusted under 35 U.S.C. 154(b) by 206 days.

(21) Appl. No.: 12/386,224

(22) Filed: Apr. 15, 2009

(65) Prior Publication Data

US 2009/0286874 A1 Nov. 19, 2009

Related U.S. Application Data (63) Continuation of application No. 11/726,176, filed on Mar. 20, 2007, now abandoned.

(60) Provisional application No. 60/784,571, filed on Mar. 22, 2006.

(51) Int. Cl.
| | |
|---|---|
| *A01N 43/08* | (2006.01) |
| *A61K 31/34* | (2006.01) |
| *A01N 37/10* | (2006.01) |
| *A61K 31/19* | (2006.01) |
| *A01N 43/00* | (2006.01) |
| *A61K 31/33* | (2006.01) |
| *A61K 8/35* | (2006.01) |
| *A61K 8/34* | (2006.01) |
| *A61K 8/36* | (2006.01) |
| *A61K 8/365* | (2006.01) |
| *A61K 8/67* | (2006.01) |
| *A61K 31/05* | (2006.01) |
| *A61K 31/07* | (2006.01) |
| *A61K 31/192* | (2006.01) |
| *A61K 31/353* | (2006.01) |
| *A61K 31/355* | (2006.01) |
| *A61K 31/375* | (2006.01) |
| *A61K 31/7048* | (2006.01) |
| *A61Q 17/04* | (2006.01) |
| *A61Q 19/08* | (2006.01) |

(52) U.S. Cl.
CPC . *A61K 8/35* (2013.01); *A61K 8/347* (2013.01); *A61K 8/36* (2013.01); *A61K 8/365* (2013.01); *A61K 8/671* (2013.01); *A61K 8/676* (2013.01); *A61K 8/678* (2013.01); *A61K 31/05* (2013.01); *A61K 31/07* (2013.01); *A61K 31/192* (2013.01); *A61K 31/353* (2013.01); *A61K 31/355* (2013.01); *A61K 31/375* (2013.01); *A61K 31/7048* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 2,134,246 | A | 10/1938 | Elger |
| 2,140,989 | A | 12/1938 | Eisenbrand |
| 2,150,140 | A | 3/1939 | Warnat |
| 2,161,651 | A | 6/1939 | Roberts et al. |
| 2,165,184 | A | 7/1939 | Pasternack |
| 2,187,467 | A | 1/1940 | Stuart |
| 2,249,903 | A | 7/1941 | Ludwig et al. |
| 2,294,937 | A | 9/1942 | Ruskin |
| 2,297,212 | A | 9/1942 | Gockel |
| 2,400,171 | A | 5/1946 | Ruskin |
| 2,442,461 | A | 6/1948 | Karrer |
| 2,585,580 | A | 2/1952 | Opplt et al. |
| 2,676,182 | A | 4/1954 | Daudt et al. |
| 2,721,161 | A | 10/1955 | Maiese |
| 3,541,205 | A | 11/1970 | Hardigan et al. |
| 3,836,437 | A | 9/1974 | Osada et al. |
| 4,199,469 | A | 4/1980 | Walzer et al. |
| 4,294,852 | A | 10/1981 | Wildnauer et al. |
| 4,367,157 | A | 1/1983 | Sherman |
| 4,372,874 | A | 2/1983 | Modrovich |
| 4,698,178 | A | 10/1987 | Huttinger et al. |
| 4,722,936 | A | 2/1988 | Jacob |
| 4,725,658 | A | 2/1988 | Thayer et al. |
| 4,818,521 | A | 4/1989 | Tamabuchi et al. |
| 4,847,071 | A | 7/1989 | Bissett et al. |
| 4,938,969 | A | 7/1990 | Schinitsky et al. |
| 4,946,671 | A | 8/1990 | Bissett et al. |
| 4,954,332 | A | 9/1990 | Bissett et al. |
| 4,983,382 | A | 1/1991 | Wilmott et al. |
| 5,023,235 | A | 6/1991 | N'Guyen et al. |

(Continued)

FOREIGN PATENT DOCUMENTS

| | | |
|---|---|---|
| EP | 0716847 | 6/1996 |
| EP | 1121926 | 8/2001 |

(Continued)

OTHER PUBLICATIONS

Suggitt, et al.; "50 Years of Preclinical Anticancer Drug Screening: Empirical to Target-Driven Approaches"; 2005; Clinical Cancer Research; 11: 971-981.*

(Continued)

*Primary Examiner* — Craig Ricci
*Assistant Examiner* — Jared D Barsky
(74) *Attorney, Agent, or Firm* — Lerner, David, Littenberg, Krumholz & Mentlik, LLP (57) ABSTRACT

An anti-aging composition containing: (a) at least one first active ingredient chosen from phloretin and its derivatives; (b) at least one second active ingredient chosen from cinnamic acid, resveratrol, retinol, ascorbic acid, tocopherol, and their derivatives; and (c) at least one non-aqueous organic solvent, with the proviso that if the composition contains ascorbic acid, water is present as a co-solvent.

9 Claims, 6 Drawing Sheets

(56) References Cited

U.S. PATENT DOCUMENTS

| | | | |
|---|---|---|---|
| 5,091,171 A | 2/1992 | Yu et al. |
| 5,140,043 A | 8/1992 | Darr et al. |
| 5,147,578 A | 9/1992 | Kirk et al. |
| 5,334,737 A | 8/1994 | Thimineur et al. |
| 5,536,500 A | 7/1996 | Galey et al. |
| 5,573,709 A | 11/1996 | Wells |
| 5,620,965 A | 4/1997 | Blank |
| 5,703,122 A | 12/1997 | Duffy |
| 5,736,567 A | 4/1998 | Cantin et al. |
| 6,146,664 A | 11/2000 | Siddiqui |
| 6,346,254 B1 | 2/2002 | Streicher et al. |
| 6,423,747 B1 | 7/2002 | Lanzendorfer et al. |
| 6,448,232 B1 | 9/2002 | Ehrenkranz |
| 6,521,271 B1 | 2/2003 | Phan |
| 6,524,599 B2 | 2/2003 | Pinnell |
| 7,179,841 B2 | 2/2007 | Zielinski et al. |
| 2002/0003454 A1 | 1/2002 | Sweeney et al. |
| 2003/0015253 A1 | 1/2003 | Gass et al. |
| 2003/0015265 A1 | 1/2003 | Jones |
| 2004/0015291 A1 | 1/2004 | Petzold et al. |
| 2005/0015405 A1 | 1/2005 | Plastina et al. |
| 2005/0154054 A1* | 7/2005 | Zielinski et al. | 514/474 |
| 2008/0233076 A1 | 9/2008 | Hansenne et al. |

FOREIGN PATENT DOCUMENTS

| | | |
|---|---|---|
| EP | 1201227 A2 | 5/2002 |
| FR | 2795319 | 12/2000 |
| FR | 2826008 A1 | 12/2002 |
| JP | 01-211529 | 2/1988 |
| JP | 2003-212774 | 7/2003 |
| JP | 2004-203835 | 7/2004 |
| WO | 0076492 | 12/2000 |
| WO | 0078283 | 12/2000 |
| WO | 0191715 | 12/2001 |
| WO | 02/19972 | 3/2002 |
| WO | 02/81027 | 10/2002 |
| WO | 2004000242 A1 | 12/2003 |
| WO | WO 2004000242 A1 * | 12/2003 |
| WO | 2005107729 | 11/2005 |

OTHER PUBLICATIONS

Castro; "Calcineurin inhibitors in the treatment of allergic dermatitis"; 2006 J. Pediatr. (Rio J.); 82(5 Suppl): S166-72.*

Mitsuharu et al.; JP 2003-212774 A; Jul. 2003; English machine translation.*

Kim et al.; "Comprehensive Study on Vitamin C Equivalent Antioxidant Capacity (VCEAC) of Various Polyphenolics in Scavenging a Free Radical and its Structural Relationship"; 2004; Critical Reviews in Food Science and Nutrition; 44: 253-273.*

Psao et al.; "Optimization of a new mobile phase to know the complex and real polyphenolic composition: towards a total phenolic index using high-performance liquid chromatography"; 2003; Journal of Chromatography A, 1018: 29-40.*

Fang et al.; Free Radicals, Antioxidants, and Nutrition; 2002; Nutrition 18:872-879.*

European Search Report for Application EP07005927.4 dated Jul. 19, 2013.

Hunter et al: "Variation in concentrations of phloridzin and phloretin in apple foliage", Phytochemistry, Pergamon Press, GB, val. 34, No. 5, Nov. 1, 1993, pp. 1251-1254, XP026631105.

European Communication dated Oct. 28, 2008 as received in corresponding European application No. 07005927.4.

Supplementary European Search Report as received in corresponding European application No. 07005927.4 dated Aug. 18, 2008.

Canadian Communication dated Nov. 17, 2008 as received in corresponding Canadian application No. 2,582,736.

Partial European Search Report as received in corresponding European application No. 07005927.4 dated May 21, 2008.

Joe A. Vinson, Yousef A. Dabbagh, Mamdouh M. Serry, Jinhee Jang, Plant flavonoids, especially tea flavonols, are powerful antioxidants using an in vitro oxidation model for heart disease, Journal of Agriculture and Food Chemistry, pp. 2800-2802, Nov. 1, 1995, No. 11, American Chemical Society, Washington DC US.

G. Paganda, N. Miller, C. A. Rice-Evans, The polyphenolic content of fruit and vegetables and their antioxidant activities. What does a serving constitute?, pp. 153-162, 1999, Free Radical Research,_ Yverdon,_Switzerland.

Lin, J. Lin, R. Gupta, J. Tournas, J. Bureh, A. Selim, N. Monteiro-Riviere, J. Grichnik, J. Zielinski, S. Pinnell: Ferulic Acid Stabilizes a Solution of Vitamins C and E and Doubles its Photoprotection of Skin, published by the Society for Investigative Dermatology, Inc., Oct. 4, 2005 (#125), pp. 826-832, The Journal of Investigative Dermatology.

Chemical Abstracts, '1 10:198950r Cosmetic skin lightening and UV-absorbing compositions containing isoferulic acid (salts), ascorbic acid (derivatives), and polyalcohols, Shiyaku, et al., vol. 110, (1989), (Pub. Nov. 1988).

Bissett, et al., 'Photoprotective effect of superoxide-scavenging antioxidants against ultraviolet radiation-induced chronic skin damage in the hairless mouse', pp. 58 and 60, Photodermatol PhotoimmunolPhotomed1990:7:pp. 58 and 60.

Brand, et al., Going with the grain. (Ingredients: Rice), Soap Perfumery & Cosmetics, 76,3, 40(4), ISSN: 0037-749X, pp. 1-6, (1993), Mar. 2003.

Buettner, et al., 'Catalytic Metals, Ascorbate and Free Radicals; Combinations to Avoid' Radiation Res. 145,532-541 (1996), Presented at the Fenton Centennial Symposium at the 42nd Annual Meeting of the Radiation Research Society, San Jose CA. Apr. 1995.

Buettner & Schafer, 'AscH2 is a Ui-Acid', Ascorbate Chemistry, Oxygen Society Education Program, Date Unkown.

Buettner & Schafer 4, Forms of Ascorbate, Ascorbate Chemistry, Oxygen Society Education Program, Date Linkown.

Buettner & Schafer 5, 'Ascorbate Falling Apart', Ascorbate Chemistry, Oxygen Society Education Program, Date Unkown.

Buettner & Schafer 6, Kinetics of AscH—Reactions Ascorbate Chemistry, Oxygen Society Education Program, Date Unkown.

Buettner & Scaffer 15, "The Pecking Order", Ascorbate Chemistry, Oxygen Society Education Program, Date Unkown.

Ciminera, et al., 'Stable Ascorbic Acid Solution for Parenteral Use' Scientific Edition, Journal of the American Pharmaceutical Association, pp. 363-365, 1946.

Cosmetics and Personal Care Market, Eastman referencing J. Am. Coil. Toxicol., 4(5), 1985.

Deutsch, 'Review Dehydroascorbic Acid' Journal of Chromatography A 881 (2000) pp. 299-307, © 2000 Elsevier Science B.V.

Diethylenglykolmonoethylether, pp. 1-2, Apr. 13, 2003 ® ab 1999 Ralf Rebmann http://.gifte.de/diethylenglykolmonoethylether.htm.

Diethylene Glycol Monoethyl Ether, H&S: Diethylene Glycol Monoethyl Ether, NTP Chemical Repository, Last Revised Aug. 13, 2001, pp. 1-8, http://ntp-dp.Niehs.nih.gov/NTP_Reports/NTP_Chem_HS_HTML/LJNTP_Cheml/Radianl 11 . . . .

Englard et al. The biochemical Functions of Ascorbic Acid, Annual Reviews Inc., 1966, pp. 365-395, 398-406.

Fox, Topical bioactive materials (part 2) Cosmetics and Toiletries, Sep. 1994. pp. 83(22), v109, n9, ISSN: 0361-4387.

'HORT64O—Metabolic Plant Physiology', Ligin biosynthesis—Secondary products derived form aromatic amino acids, Aug. 20, 2003, pp. 1-3, http://www.hort.purdue.edu/rhodev/hort640c/secprod/se00016.htm.

Imai, et al ., The Antiscorbutic Activity of L-Ascorblc Acid Phosphate Given Orally and Percutaneously in Guinea Pigs, The Japanese Journal of Pharmacology, vol. 17, No. 2. Jun. 1967.pp. 317-324.

Increasing use of high sun protection factors in sunscreen products, printed Sep. 15, 2003, 2 pages_http://wv.w.roche.com/pages/facets/1/uvfllte.htm.

Kunert et al., The Effect of Vitamin C on in nino Lipid Peroxidation in Guinea Pigs as measured by Pentane and Ethane production, Lipids, vol. 18, No. 4. (1983), pp. 271-274.

Lewin, "Vitamin C: Its Molecular Biology and Medical Potential", Academic Press, 1976, pp. 4-63,196-223.

Lin, LJV photoprotection by combination topical antioxidants vitamin C and vitamin E @2003 American Academy of Dermatology, Inc., J Am Acad Dermatol, pp. 866-874, vol. 46, No. 6.

(56) References Cited

OTHER PUBLICATIONS

Lu, 'Interactions of lipoic acid radical cations with vitamin C and Vitamin E analogue and hydroxycinnamic acid derivatives' Archives of Biochemistry and Biophysics 406,© 2002 Elsevier Science (USA), pp. 78-84, Academic Press.
Merck & Co., Inc. 'Ascorbic Acid Vitamin C in wound Healing', Annotated Bibliography, pp. 1-15 Merck_Service_Bulletin,_Mar. 1941.
Pinnell. Cutaneous photodamage, oxidative stress, and topical antioxidant protection Continuing Medical Education from Duke University Medical Center. © 2003 by American Academy of Dermatology, Inc., pp. 1-22, Jam Acad Dermatol, vol. 46, No. 1.
Pinnell, 'Topical L-Ascorbic Acid: Percutaneous Absorption Studies' Dermatol. Surg. 2001; 27:137-142 © Feb. 2001 by the American Society for Dermatologic Surgery, Inc., pp. 137-142, published by_Blackwell_Science,_Inc._ISSN:_1076-0512/01.
Propanediol_by_HyperDictionary.com_©_2000-2003_ Webnox_Corp.
Propylene glycol, The Chemistry Store,com, http://www.chemistrystore.com/propylene_glycol.htm2002.
Rice-Evans, Structure-Antioxidant Activity Relationship of Flavonoids and Phenolic Acids Review Article, Free Radical Biology & Medicine, pp. 933, 948-953, vol. 20, No. 7, © 1996 Elsevier Science, Inc.
Safety (MSDS) data for 1 ,2-propanediol, pp. 1-2, Updated Sep. 4, 2003 http:i/ptcl.chem..ox.ac.ukIMSDS/PRII ,2-propanedio.html.
Saija, 'In vitro and in vivo evaluation of caffeic andferulic acids as topical photoprotective agents', International Journal of Pharmaceutics, pp. 39-47 © 2000, Elsevier Science, Inc.
Schaefer et al., 'pH dependence', pp. 739-740, Skin Permeability, Springer-Verlang Berlin Heidelberg New York 1982.
Takashima, et al., 'Ascorbic Acid Esters and Skin Pigmentation', American Perfumer and Cosmetics,_vol. 86._No. 7, _Jul. 1971,_ pp. 29-36.
Meucci et al., 'Ascorbic Acid Stability in Aqueous Solutions', Acta Vitaminol.Enzymol.. 1985, 7(3-4) pp. 147-154.
Transcutol® P and Transcutol® HP, printed Sep. 19, 2003, http://ew.gattefosse.com/pharma/products/transcup.htni.
Vitamin-C Science, printed Sep. 15, 2003, http://www.skinceuticals.cornlscience/vitaminc.html.
A. Chardon, D. Moyal, C. Hourseau: Persistent pigment darkening response as a method for evaluation of UVA protection assays published in 'Sunscreens: development, evaluation and regulatory aspects', 2nd edition (edited by N. Lowe, N. Shath, M. Pathak, ed.; Marcel Dekker Inc. -270_Madison Avenue,_New York, NY 10016), pp. 559-582,_1986.
CTFA Cosmetic Ingredient Handbook; 2nd edition; 1992; p. 582; published by The Cosmetic Toiletry and Fragrance Association, Inc. 11011 7th Street NW, Suite 300, NW Washington, D.C.20036.
D. Moyal, A. Chardon, N. Kollias: UVA protection efficacy of sunscreens can be determined by the persistent pigment darkening (PPD) method (Part 2), published in Photo-dermatol, PhotoImmunol. Photomed., 16, pp. 250-255, 2000, printed in Denmark.
Lupo "Antioxidants and vitamins in cosmetics," Clinics in Dermatology, vol. 19, Issue 4, Jul.-Aug. 2001, pp. 467-473.
Darr et al "Topical vitamin C protects porcine skin from ultraviolet radiation-induced damage," Br. J. Dermatology, 127 (3): 247-253, 1992.
U.S. Appl. No. 21/132,662.

* cited by examiner

ANTI-AGING COMPOSITION CONTAINING PHLORETIN

CROSS-REFERENCE TO RELATED APPLICATIONS

This application is a continuation, of U.S. application Ser. No. 11/726,176, filed on Mar. 20, 2007, which is a nonprovisional of a provisional Application No. 60/784,571, filed on Mar. 22, 2006.

BACKGROUND OF THE INVENTION

Aging skin is the result of more than just chronological age. Skin is exposed to environmental elements that cause radicals to form in the skin. These radicals attack the collagen layer of the skin and break it down, causing lines and wrinkles to appear. This process is commonly called photo-aging. Diseases and disorders of skin that also may result from radical damage include skin cancer, skin irritation or inflammation, dermatitis, allergy, psoriasis, acne, eczema, rosacea.

Application of antioxidants can help prevent radical-induced damage in skin. Applying Vitamin C, for example, to the skin can provide antioxidant protection, prevent photo-aging, and stimulate collagen production. However, not all Vitamin C formulations produce these benefits due to lack of stability.

The present invention is thus directed to a composition and process for inhibiting radical-induced damage to skin which does not suffer from conventional stability issues.

BRIEF SUMMARY OF THE INVENTION

The present invention is directed to an anti-aging composition containing:

(a) at least one first active ingredient chosen from phloretin and its derivatives;

(b) at least one second active ingredient chosen from cinnamic acid, resveratrol, retinol, ascorbic acid, tocopherol, and their derivatives; and (c) at least one non-aqueous organic solvent, and with the proviso that, if the composition contains ascorbic acid, water is present as a co-solvent.

The present invention is also directed to a process for treating radical-induced damage to skin by contacting the skin with the above-disclosed composition.

DETAILED DESCRIPTION OF THE INVENTION

Other than in the operating examples, or where otherwise indicated, all numbers expressing quantities of ingredients and/or reaction conditions are to be understood as being modified in all instances by the term "about".

The present invention is directed to the surprising discovery that by combining at least one first active ingredient chosen from phloretin, and its derivatives, with at least one second active ingredient chosen from cinnamic acid, resveratrol, retinol, ascorbic acid, tocopherol and their derivatives, an effective treatment for radical-induced damage to skin is realized.

First Active Ingredient

Phloretin is the aglucone portion of phlorizin and is a polyphenolic compound. It is split from phlorizin by acid hydrolysis. Alternatively, phloretin can be completely synthesized directly by known processes.

Suitable phloretin derivatives include, but are not limited to, dihydrochalcone derivatives, such as those disclosed in U.S. Pat. No. 6,448,232, the entire contents of which is hereby incorporated by reference.

The composition of the present invention contains the at least one first active ingredient in an amount of from about 0.1 to about 10% by weight, such as from about 0.5 to about 7% by weight, such as from about 1 to about 5% by weight, such as from about 0.5 to about 3% by weight, such as from about 1 to about 2% by weight, all weights based on the total weight of the composition.

Second Active Ingredient

The at least one second active ingredient is chosen from cinnamic acid, resveratrol, retinol, ascorbic acid, tocopherol, and their derivatives.

In one embodiment, the at least one second active is a cinnamic acid derivative, examples of which include, but are not limited to, caffeic acid, p-coumaric acid, ferulic acid, sinapinic acid, mixtures thereof, cis and trans isomers thereof, salts thereof, and equivalent derivatives thereof.

In a particularly preferred embodiment, the at least one second ingredient is a combination of ferulic acid and ascorbic acid.

The at least one second active ingredient is present in the composition in an amount of from about 0.1 to about 25% by weight, such as from about 0.2 to about 15% by weight, such as from about 0.2 to about 10% by weight, all weights based on the total weight of the composition.

The ratio by weight of first active ingredient to second active ingredient will typically be from about 0.1:10 to about 10:0.1, such as about 0.3:5, such as about 0.5:2.

Non-Aqueous Organic Solvent

Any non-aqueous organic solvent capable of solubilizing the first and second active ingredients may be employed. Examples of suitable solvents include, but are not limited to, non-aqueous polar organic solvents, and non-aqueous non-polar organic solvents.

Non-Aqueous Polar Organic Solvent

A variety of non-aqueous polar organic solvents may be used in the anti-aging composition of the present invention. Examples thereof are as follows.

Polyols

Polyols are suitable non-aqueous polar organic solvents. For purposes of this specification, polyols are defined as compounds which contain three or more hydroxyl groups per molecule. Examples of suitable polyols include glucose glutamate, glycerin, 1,2,6-hexanetriol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, sorbeth-6, sorbeth-20, sorbeth-30, sorbeth-40, thioglycerin, and mixtures thereof. An especially preferred polyol is glycerin.

Polymeric or Monomeric Ethers

Also suitable as the non-aqueous polar organic solvent are homopolymeric or block copolymeric liquid ethers. Polymeric ethers are preferably formed by polymerization of monomeric alkylene oxides, generally ethylene or propylene oxides. Examples of such polymeric ethers include PEG, PPG, and derivatives thereof.

Other examples of suitable polymeric ethers include polyoxypropylene polyoxyethylene block copolymers. Such compounds are sold under the CTFA name Meroxapol 105, 108, 171, 172, 174, 178, 251, 252, 254, 255, 258, 311, 312, and 314.

Mono- and Dihydric Alcohols

Also suitable for use as to the non-aqueous polar organic solvent are mono- and dihydric alcohols of the general formula $R(OH)_n$ where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, 1,5-pentanediol, triethylene glycol, dipropylene glycol, and mixtures thereof.

Sorbitan Derivatives

Sorbitan derivatives, which are defined as ethers or esters of sorbitan, are also suitable polar solvents. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

Non-Aqueous Non-Polar Organic Solvents

A variety of non-aqueous non-polar organic solvents can be used in the composition of the invention, if so desired. Examples thereof are as follows.

Silicones

Silicones are suitable non-polar compounds. The silicones may be volatile or non-volatile. The term "volatile" means that the silicone has a measurable vapor pressure, i.e. a vapor pressure of at least 2 mm. of mercury at 20° C. If volatile, the silicone generally will have a viscosity of 0.5 to 25 centistokes at 25° C. Suitable volatile silicones include cyclic silicones, linear silicones, or mixtures thereof.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

The silicone may also be nonvolatile, and in particular water insoluble nonvolatile silicones. The term "nonvolatile" means that the silicone has a vapor pressure of less than 2 mm. of mercury at 20° C. A variety of silicones fits this definition including dimethicone, phenyl trimethicone, diphenyl dimethicone, methicone, hexadecyl methicone, stearoxydimethicone, stearyl dimethicone, cetyl dimethicone, and so on.

Cyclomethicone is a preferred silicone for use in the composition of the invention.

Esters

In addition to the sorbitan esters, other esters are also suitable as the non-aqueous non-polar organic solvent. In general such esters have the formula $R^1CO—OR^2$ wherein $R^1$ and $R^2$ are independently a $C_{1-25}$ straight or branched chain saturated or unsaturated alkyl, alkylcarbonyloxyalkyl, or alkoxycarbonylalkyl, aryl, which may be substituted or unsubstituted with halogen, hydroxyl, alkyl, and the like.

Examples of suitable esters include alkyl acetates, alkyl behenates, alkyl lactates, alkyl benzoates, alkyl octanoates, alkyl salicylates, and in particular $C_{12-15}$ alkyl benzoate. Examples of further esters are set forth on pages 502-506 of the CTFA Cosmetic Ingredient Handbook, Second Edition, 1992, which is hereby incorporated by reference.

Fats and Oils

Fats and oils are also suitable as the non-aqueous non-polar organic solvent. Preferably these materials are liquids or semi-solids at room temperature. They are generally defined as glyceryl esters of fatty acids (triglycerides), as well as the synthetically prepared esters of glycerin and fatty acids. Examples of such materials include oils such as apricot kernel oil, avocado oil, canola oil, olive oil, sesame oil, peanut oil, soybean oil, trilinolenin, trilinolein, trioctanoin, tristearin, triolein, sesame oil, rapeseed oil, sunflower seed oil, and so on.

Fatty Acids

Fatty acids are also suitable as the non-aqueous non-polar organic solvent in the compositions of the invention. Preferably the fatty acids are liquid or semi solid at room temperature. Fatty acids are the carboxylic acids obtained by hydrolysis of animal or vegetable fats and oils. Carboxylic acids having alkyl chains shorter than about seven carbon atoms are not generally considered fatty acids. Fatty acids have the general structure $R^3$—COOH where $R^3$ is a straight or branched chain saturated or unsaturated $C_{7-65}$ alkyl. Examples of suitable fatty acids include arachidic acid, arachidonic acid, behenic acid, capric acid, caproic acid, caprylic acid, coconut acid, corn acid, cottonseed acid, hydrogenated coconut acid, hydroxystearic acid, lauric acid, linoleic acid, linolenic acid, linseed acid, myristic acid, oleic acid, palmitic acid, palm kernel acid, soy acid, tallow acid, and the like.

Fatty Alcohols

Fatty alcohols may also be used as the non-aqueous non-polar organic solvent. Fatty alcohols are generally made by reducing the fatty acid —COOH group to the hydroxyl function. They generally have the formula $R^4CH_2OH$. Examples of fatty alcohols are behenyl alcohol, $C_{9-11}$ alcohol, $C_{12-13}$ alcohol, $C_{12-15}$ alcohol, $C_{12-16}$ alcohol, caprylic alcohol, cetearyl alcohol, cetyl alcohol, coconut alcohol, decyl alcohol, lauryl alcohol, myristyl alcohol, oleyl alcohol, and the like.

Hydrocarbons

Hydrocarbons are also good non-aqueous non-polar organic solvents in accordance with the invention. Examples of suitable hydrocarbons include $C_{7-60}$ isoparaffins, ethane, heptane, hexane, hydrogenated polyisobutene, isobutane, isododecane, isoeicosane, isohexadecane, isopentane, microcrystalline wax, mineral oil, mineral spirits, paraffin, petrolatum, petroleum distillates, squalene, polyethylene, and mixtures thereof. Preferred hydrocarbons are mineral oil and polyethylene.

Lanolin and Lanolin Derivatives

Also suitable as the non-aqueous non-polar organic solvent are lanolin and derivatives thereof. Examples of such materials include acetylated hydrogenated lanolin, acetylated lanolin alcohol, laneth, lanolin acid, lanolin oil, lanolin alcohol, lanolin wax, and so on.

The composition of the present invention contains at least one organic solvent in an amount of from about 1 to about 95% by weight, such as from about 1 to about 60% by weight, such as from about 5 to about 40% by weight, all weights based on the total weight of the composition.

In the event that ascorbic acid is employed in the composition of the present invention as a second active ingredient, water will be present in the composition as a co-solvent. The water will be employed in an amount at least sufficient to solubilize the ascorbic acid present in the composition.

In a preferred embodiment of the present invention, the composition is in the form of a single-phase solution, such as cosmetic serums or aerosols, for example. In another embodiment, the composition is in the form of an emulsion, such as creams or lotions, for example.

Other Ingredients

It may also be desired to include certain other ingredients in the composition of the invention, such as surfactants, waxes, colorants, preservatives, and the like.

Surfactants

Silicone Surfactants

The term "surfactant" is defined, in accordance with the invention, as a compound having at least one hydrophilic moiety and at least one lipophilic moiety. The surfactants may be silicone surfactants (also referred to as organosiloxane emulsifiers) or organic surfactants.

Suitable silicone surfactants used in the compositions of the invention may be liquid or solid at room temperature and are generally a water-in-oil or oil-in-water type surfactants which are preferably nonionic, having an Hydrophile/Lipophile Balance (HLB) of 2 to 18. Preferably the organosiloxane is a nonionic surfactant having an HLB of 2 to 12; such as 2 to 10; such as 4 to 6. The HLB of a nonionic surfactant is the balance between the hydrophilic and lipophilic portions of the surfactant and is calculated according to the following formula:

$$HLB = 20(1 - S/A)$$

where S is the saponification number of the surfactant and A is the acid number of the surfactant.

The silicone surfactant or emulsifier used in the compositions of the invention is a polymer containing a polymeric backbone including repeating siloxy units that may have cyclic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will confer lipophilicity are $C_{1-40}$ straight or branched chain alkyl, fluoro, aryl, aryloxy, $C_{1-40}$ hydrocarbyl acyl, hydroxypolypropyleneoxy, or mixtures thereof. The $C_{1-40}$ alkyl may be non-interrupted, or interrupted by one or more oxygen atoms, a benzene ring, amides, esters, or other functional groups.

Organosiloxane polymers useful in the compositions of the invention include those sold by Goldschmidt under the ABIL™ trademark including ABIL B-9806™, as well as those sold by Rhone-Poulenc under the Alkasil™ tradename. Also, organosiloxane emulsifiers sold by Amerchol under the Amersil™ tradename, including Amersil ME-358™, Amersil DMC-287™ and Amersil DMC-357™ are suitable. Dow Corning surfactants such as Dow Corning 3225™ Formulation Aid, Dow Corning 190™ Surfactant, Dow Corning 193™ Surfactant, Dow Corning Q2-5200™, and the like are also suitable. In addition, surfactants sold under the tradename Silwet™ by Union Carbide, and surfactants sold by Troy Corporation under the Troysol™ tradename, those sold by Taiwan Surfactant Co. under the tradename Ablusoft™, those sold by Hoechst under the tradename Arkophob™, are also suitable for use in the invention.

Also suitable as surfactants are various organic surfactants such as anionic, nonionic, amphoteric, zwitterionic, or cationic surfactants.

The composition of the present invention may contain at least one surfactant in an amount of from about 0.01 to about 15% by weight, such as from about 0.5 to about 10% by weight, such as from about 1 to about 8% by weight, all weights based on the total weight of the total composition.

Waxes

Suitable waxes have a melting point of from about 35 to about 120° C., include animal waxes, plant waxes, mineral waxes, silicone waxes, synthetic waxes, and petroleum waxes.

The composition of the present invention may contain waxes in an amount of from about 0.1 to about 25% by weight, such as from about 0.5 to about 20% by weight, such as from about 1 to about 15% by weight, all weights based on the total weight of the total composition.

Branched Chain Silicone Resins

It may be desirable to include one or more branched chain silicone resins in the compositions of the invention. Examples of suitable silicone resins include, but are not limited to, siloxy silicate polymers such as those commercially available from GE silicones under the trade name of SR1000™, and silicone esters such as those commercially available from General Electric under the tradenames SF1318™ and SF1312™, and the like.

The composition of the present invention may contain branched chain silicone resins in an amount of from about 0.001 to about 20% by weight, such as from about 0.01 to about 15% by weight, such as from about 0.1 to about 10% by weight, all weights based on the total weight of the composition.

Pigments and Powders

Pigments and/or powders may be used in the composition of the present invention. If used, they may be present in an amount of from about 0.001 to about 35% by weight, such as from about 0.01 to about 20% by weight, such as from about 0.1 to about 10% by weight, all weights based on the total weight of the composition.

Sunscreens

The composition of the present invention may also contain a sunscreen. If used, they may be present in an amount of from about 0.001 to about 20% by weight, such as from about 0.01 to about 10% by weight, such as from about 0.05 to about 8% by weight, all weights based on the total weight of the composition.

Preservatives

A variety of preservatives may also be employed in an amount of from about 0.0001 to about 8% by weight, such as from about 0.001 to about 6% by weight, such as from about 0.005 to about 5% by weight, all weights based on the total weight of the composition.

Vitamins

The compositions of the invention may contain vitamins and/or coenzymes. Suitable vitamins include, but are not limited to, the B vitamins such as thiamine, riboflavin, pyridoxin, as well as coenzymes such as thiamine pyrophoshate, flavin adenin dinucleotide, folic acid, pyridoxal phosphate, tetrahydrofolic acid. Also Vitamin A and derivatives thereof are suitable such as retinoic acid and retinaldehyde. Additional examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

The composition of the present invention may contain vitamins and/or coenzymes in an amount of from about 0.001 to about 10% by weight, such as from about 0.01 to about 8% by weight, such as from about 0.05 to about 5% by weight, all weights based on the total weight of the composition.

Alpha or Beta Hydroxy Acids, Alpha Keto Acids

It may also be desired to add one or more alpha or beta hydroxy acids or alpha ketoacids to the compositions of the invention. Suitable alpha hydroxy acids may exist in the keto acid form, or the ester form. Examples of such alpha hydroxy acids include, but are not limited to, glycolic acid, malic acid, pyruvic acid, mandelic acid, lactic acid, methyllactic acid.

Also beta hydroxy acids such as salicylic acid, and derivatives thereof may be included in the compositions of the invention.

The composition of the present invention may contain alpha or beta hydroxy acids, or alpha keto acids in an amount of from about 0.01 to about 20% by weight, such as from about 0.1 to about 15% by weight, such as from about 0.5 to about 10% by weight, all weights based on the total weight of the composition.

According to one embodiment of the present invention, there is provided an anti-aging composition containing: (a) from about 0.1 to about 10% by weight, preferably from about 0.3 to about 5% by weight of phloretin; (b) from about 0.1 to about 10% by weight, preferably from about 0.2 to about 5% by weight of ferulic acid; (c) from about 1 to about 25% by weight, preferably from about 5 to about 20% by weight of ascorbic acid; (d) from about 1 to about 60% by weight, preferably from about 5 to about 40% by weight of a glycol; and (e) remainder, water, all weights based on the total weight of the composition.

Methods of Use

The present invention is also directed to a process for treating radical-induced damage to skin by contacting the skin with the above-disclosed composition. Treating, as used herein, means prophylactic and/or therapeutic treatment of a subject. "Prophylactic" treatment is a treatment administered to a subject who does not have symptoms of radical-induced damage or has early signs of such damage, or anticipates being exposed to situations having risk of radical-induced damage. "Therapeutic" treatment is a treatment administered to a subject who has signs of radical-induced damage.

The present invention is further described in terms of the following non-limiting examples. Unless otherwise indicated, all parts and percentages are on a weight-by-weight percentage basis.

EXAMPLES

The following products were made:
Set 1

Example A

2% Phloretin

| Ingredient | w/w % |
| --- | --- |
| Phenoxyethanol | 1.0 |
| Pentylene Glycol | 20.0 |
| Pentylene Glycol | 10.0 |
| Phloretin | 2.0 |
| Alcohol Denat. | 10.0 |
| Water | 56.9 |
| Sodium Hyaluronate | 0.1 |
| Total | 100.0 |

Example B

15% Vitamin C

| Ingredient | w/w % |
| --- | --- |
| Phenoxyethanol | 1.0 |
| Ascorbic Acid | 15.0 |
| Pentylene Glycol | 20.0 |
| Propylene Glycol | 10.0 |
| Alcohol Denat. | 10.0 |
| Water | 43.9 |
| Sodium Hyaluronate | 0.1 |
| Total | 100.0 |

Example C

Control Formulation

| Ingredient | w/w % |
| --- | --- |
| Phenoxyethanol | 1.0 |
| Pentylene Glycol | 20.0 |
| Propylene Glycol | 10.0 |
| Alcohol Denat. | 10.0 |
| Water | 58.9 |
| Sodium Hyaluronate | 0.1 |
| Total | 100.0 |

Example D

Ferulic Acid 0.5%, Phloretin 2%

| Ingredient | w/w % |
| --- | --- |
| Ferulic Acid | 0.5 |
| Phenoxyethanol | 1.0 |
| Pentylene Glycol | 20.0 |
| Propylene Glycol | 10.0 |
| Phloretin | 2.0 |
| Alcohol Denat. | 10.0 |
| Water | 56.4 |
| Sodium Hyaluronate | 0.1 |
| Total | 100.0 |

Example E

15.3% Vitamin C, 0.5% Ferulic Acid, 1.0% Vitamin E

| Ingredient | w/w % |
| --- | --- |
| Phenoxyethanol | 1.05 |
| Pentylene Glycol | 5.00 |
| Propylene Glycol | 5.00 |
| Glycerin | 3.00 |
| Ascorbic acid | 15.30 |
| Vitamin E | 1.00 |
| Ferulic acid | 0.50 |
| Water | 65.87 |
| Sodium Hyaluronate | 0.10 |
| Antifoam | 0.01 |
| Laureth-23 | 3.00 |
| Sodium Hydroxide (to pH 3) | 0.18 |
| Total | 100.00 |

Example F

15.3% Vitamin C, 0.5% Ferulic Acid, and 2% Phloretin

| Ingredient | w/w % |
| --- | --- |
| Ferulic Acid | 0.5 |
| Phenoxyethanol | 1.0 |
| Ascorbic Acid | 15.0 |
| Pentylene Glycol | 20.0 |
| Propylene Glycol | 10.0 |
| Phloretin | 2.0 |
| Alcohol Denat. | 10.0 |
| Water | 41.4 |
| Sodium Hyaluronate | 0.1 |
| Total | 100.0 |

Set 2

Example G

15% Vitamin C, 0.5% Ferulic Acid, 2% Phloretin, and 0.02% Vitamin E

| Ingredient | w/w % |
| --- | --- |
| Phenoxyethanol | 1.00 |
| Pentylene Glycol | 20.00 |
| Propylene Glycol | 10.00 |
| Alcohol Denat. | 10.00 |
| Ascorbic acid | 15.00 |
| Ferulic acid | 0.50 |
| Phloretin | 2.00 |
| Vitamin E | 0.02 |
| Water | 41.38 |
| Sodium Hyaluronate | 0.10 |
| Total | 100.00 |

Example H

15% Vitamin C, and 2% Phloretin

| Ingredient | w/w % |
| --- | --- |
| Phenoxyethanol | 1.0 |
| Pentylene Glycol | 20.0 |
| Propylene Glycol | 10.0 |
| Alcohol Denat. | 10.0 |
| Ascorbic acid | 15.0 |
| Phloretin | 2.0 |
| Water | 41.9 |
| Sodium Hyaluronate | 0.10 |
| Total | 100.0 |

Example I

0.5% Ferulic Acid

| Ingredient | w/w % |
| --- | --- |
| Phenoxyethanol | 1.0 |
| Pentylene Glycol | 20.0 |
| Propylene Glycol | 10.0 |
| Alcohol Denat. | 10.0 |
| Ferulic acid | 0.5 |
| Water | 58.4 |
| Sodium Hyaluronate | 0.10 |
| Total | 100.0 |

Example J

Control Formulation

| Ingredient | w/w % |
| --- | --- |
| Phenoxyethanol | 1.0 |
| Pentylene Glycol | 20.0 |
| Propylene Glycol | 10.0 |

-continued

| Ingredient | w/w % |
| --- | --- |
| Alcohol Denat. | 10.0 |
| Water | 58.9 |
| Sodium Hyaluronate | 0.1 |
| Total | 100.0 |

Example K

15% Vitamin C, 1% Vitamin E, and 0.5% Ferulic Acid

| Ingredient | w/w % |
| --- | --- |
| Phenoxyethanol | 1.05 |
| Pentylene Glycol | 5.00 |
| Propylene Glycol | 5.00 |
| Glycerin | 3.00 |
| Ascorbic acid | 15.30 |
| Vitamin E | 1.00 |
| Ferulic acid | 0.50 |
| Water | 65.87 |
| Sodium Hyaluronate | 0.10 |
| Antifoam | 0.01 |
| Laureth-23 | 3.00 |
| Sodium Hydroxide (to pH 3) | 0.18 |
| Total | 100.00 |

Example L

15% Vitamin C, 0.5% Ferulic Acid, and 2% Phloretin

| Ingredient | w/w % |
| --- | --- |
| Phenoxyethanol | 1.0 |
| Pentylene Glycol | 20.0 |
| Propylene Glycol | 10.0 |
| Alcohol Denat. | 10.0 |
| Ascorbic acid | 15.0 |
| Ferulic acid | 0.5 |
| Phloretin | 2.0 |
| Water | 41.4 |
| Sodium Hyaluronate | 0.1 |
| Total | 100.0 |

A single application of each of the samples was applied on the back of 10 subjects with very fair or fair skins (6 and 4 subjects respectively) associated with a phototype II.

All products were applied at a rate of 4 mg/cm², with a finger provided with a finger cot.

One hour and a half after application, the treated zones were exposed to 320-440 nm UVA at a dose corresponding to 2 Individual Minimal Erythemal Doses (iMED).

Colorimetric measurements and visual assessments were performed 2 hours after exposure in order to evaluate the intensity of UVA-induced erythema and that of the Persistent Pigment Darkening (PPD).

Colorimetric Measurements

The equipment used for calorimetric measurements was as follows:

MINOLTA CR 300 N°2 COLORIMETER

1600 Watts Xenon lamp ORIEL 4×4 with filters WG 335 3 mm (A) and dichroic mirror for UVA spectrum in the field 320-440 nm, was used for calorimetric measurements in compliance with the in vivo PPD method as described in the following articles: A. Chardon, D. Moyal, C. Hourseau: Persistent pigment darkening response as a method for evaluation of UVA protection assays published in "Sunscreens: development, evaluation and regulatory aspects", 2nd edition (N. Lowe, N. Shath, M. Pathak, ed.; Marcel Dekker Inc.), pp. 559-582, 1986, and D. Moyal, A. Chardon, N. Kollias: UVA protection efficacy of sunscreens can be determined by the persistent pigment darkening (PPD) method (Part 2), published in Photo-dermatol. Photoimmunol. Photomed., 16, 250-255, 2000.

UV-METER PMA N°5 with UVA Sensor SN 2423 used to measure and calculate the amounts of UVA received (J.cm²).

Balance

Finger cot

Evaluation Criteria

Colorimetric measurements were performed on the treated exposed zones (TEZ) and on the non-treated exposed zones (NTEZ) (2 measurements in triplicate). The measurements were expressed as L*, a*, and b* values (CIE 1976 L*a*b* also known as CIELAB). The L*, a*, and b* values obtained from the zones treated with a product were compared to the L*, a*, and b* values obtained from the zones treated with the control formulation.

The UVA-induced erythema is expressed as $\Delta a^*$, which represents the difference in a* values between the treated exposed zones (TEZ) and the non-treated exposed zones (NTEZ). $\Delta a^*$ represents the red hue, which quantifies the intensity of the UVA-induced erythema. The larger the $\Delta a^*$, the more intense the erythema.

Visual assessments of the UVA-induced erythema were performed 2 hours after exposure, and reported on a scale having 14 levels of evaluation, from 0=no pink color observed (no erythema) to 13=darkest pink color observed.

The Persistent Pigment Darkening (PPD) is reported as $\Delta E$, which represents the total modification of the coloring of the skin.

$\Delta E$ is expressed as the square root of $(\Delta a^{*2}+\Delta b^{*2}+\Delta L^{*2})$ The larger the $\Delta E$, the more intense the persistent pigment darkening (PPD). $\Delta E$ may be used to represent the overall change in color.

Results

Set 1

Colorimetric Measurement of UVA Induced Erythema

Figure 1:
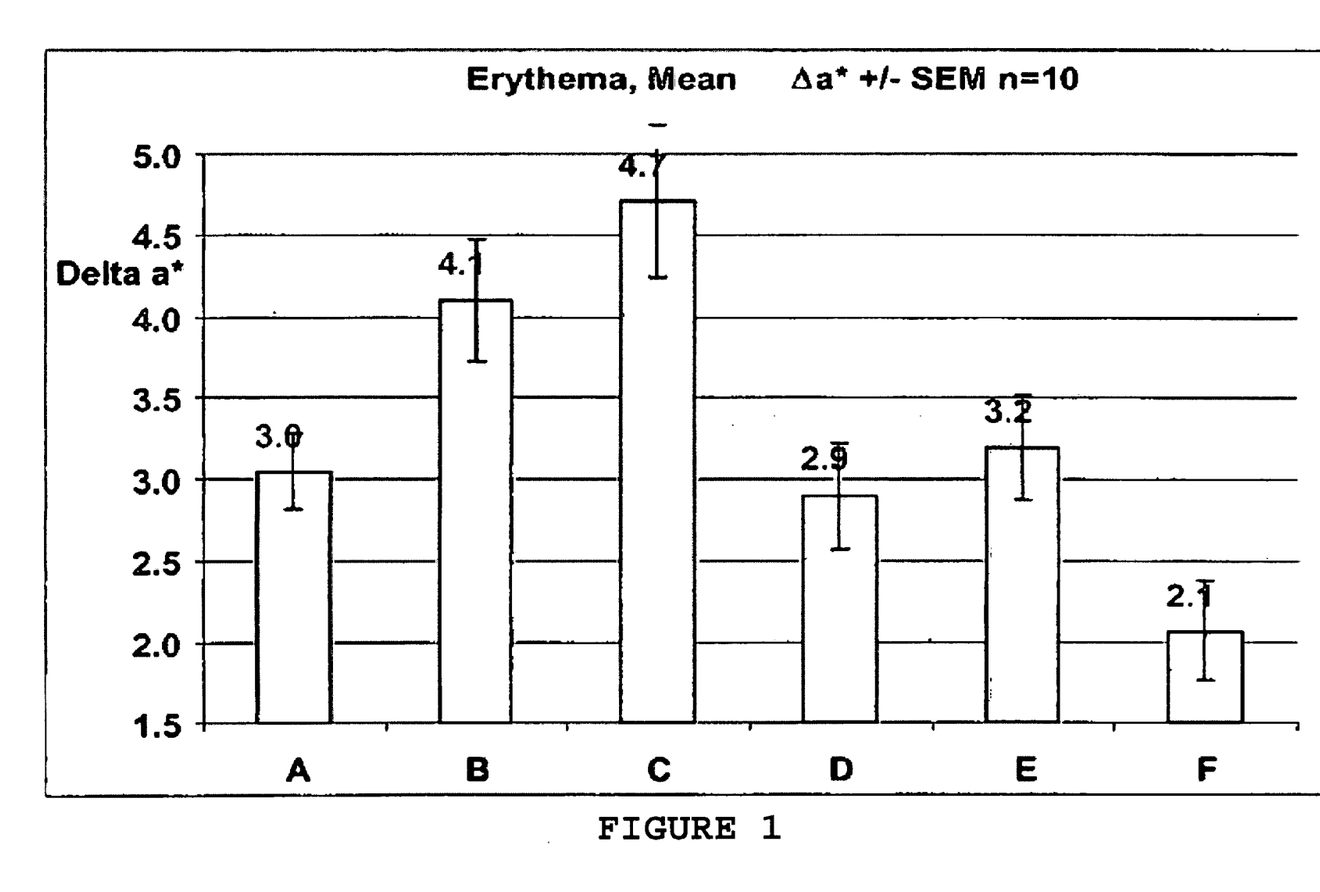
FIG. 1 shows the results of colormetric measurement of UVA induced erythema for samples A-F.

Each sample was measured against sample C, which is the control formulation containing only the carrier and no active. Referring to FIG. 1, the following results were observed.

Sample A, containing 2% phloretin, significantly reduced the intensity of the UVA induced erythema (p=0.013).

Sample B, containing 15% vitamin C, did not significantly reduced intensity of the UVA induced erythema (p=0.240).

Sample D, containing 2% phloretin and 0.5% ferulic acid, significantly reduced the intensity of the UVA induced erythema (p=0.007).

Sample E, containing 15.3% Vitamin C, 0.5% ferulic acid and 1% Vitamin E, significantly reduced the intensity of the UVA induced erythema (p=0.023).

Sample F, containing 2% phloretin, 0.5% ferulic acid and 15.3% vitamin C, significantly reduced the intensity of the UVA induced erythema (p=0.001).

Visual Assessment of UVA Induced Erythema

Figure 2:
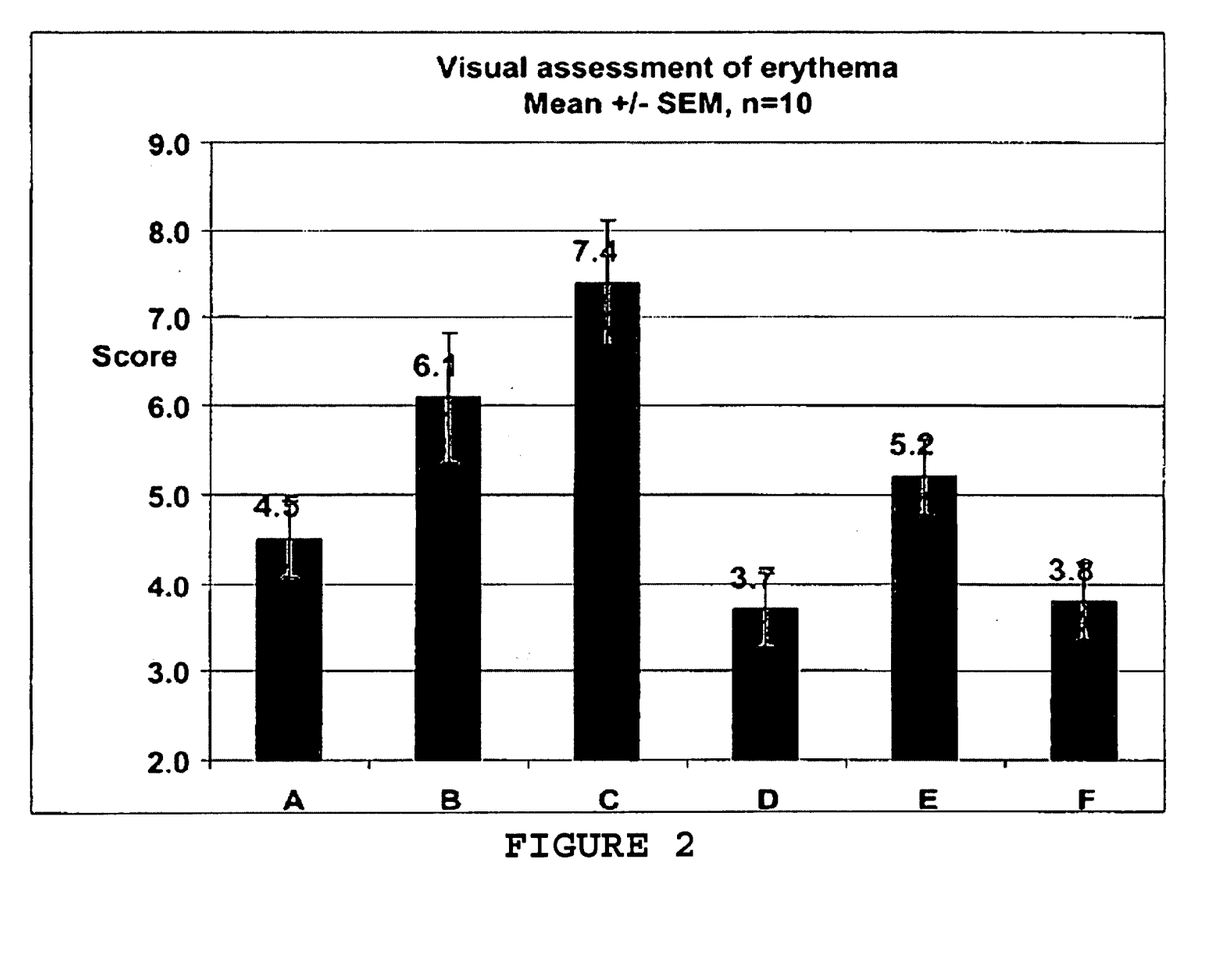
FIG. 2 shows the results of visual assessment of UVA induced erythema for samples A-F.

Each sample was measured against sample C, which is the control formulation containing only the carrier and no active. Referring to FIG. 2, the following results were observed.

Sample A, containing 2% phloretin, visually significantly reduced the intensity of the UVA erythema (p=0.018).

Sample B, containing 15% vitamin c, visually significantly reduced the intensity of the UVA erythema (p=0.033).

Sample D, containing 2% phloretin and 0.5% ferulic acid, visually significantly reduced the intensity of the UVA erythema (p=0.002).

Sample E, containing 15.3% Vitamin C, 0.5% ferulic acid and 1% Vitamin E visually significantly reduced the intensity of the UVA erythema (p=0.004).

Sample F, containing 2% phloretin, 0.5% ferulic acid and 15.3% vitamin C, visually significantly reduced the intensity of the UVA erythema (p=0.006).

Persistent Pigment Darkening (PPD)

Figure 3:
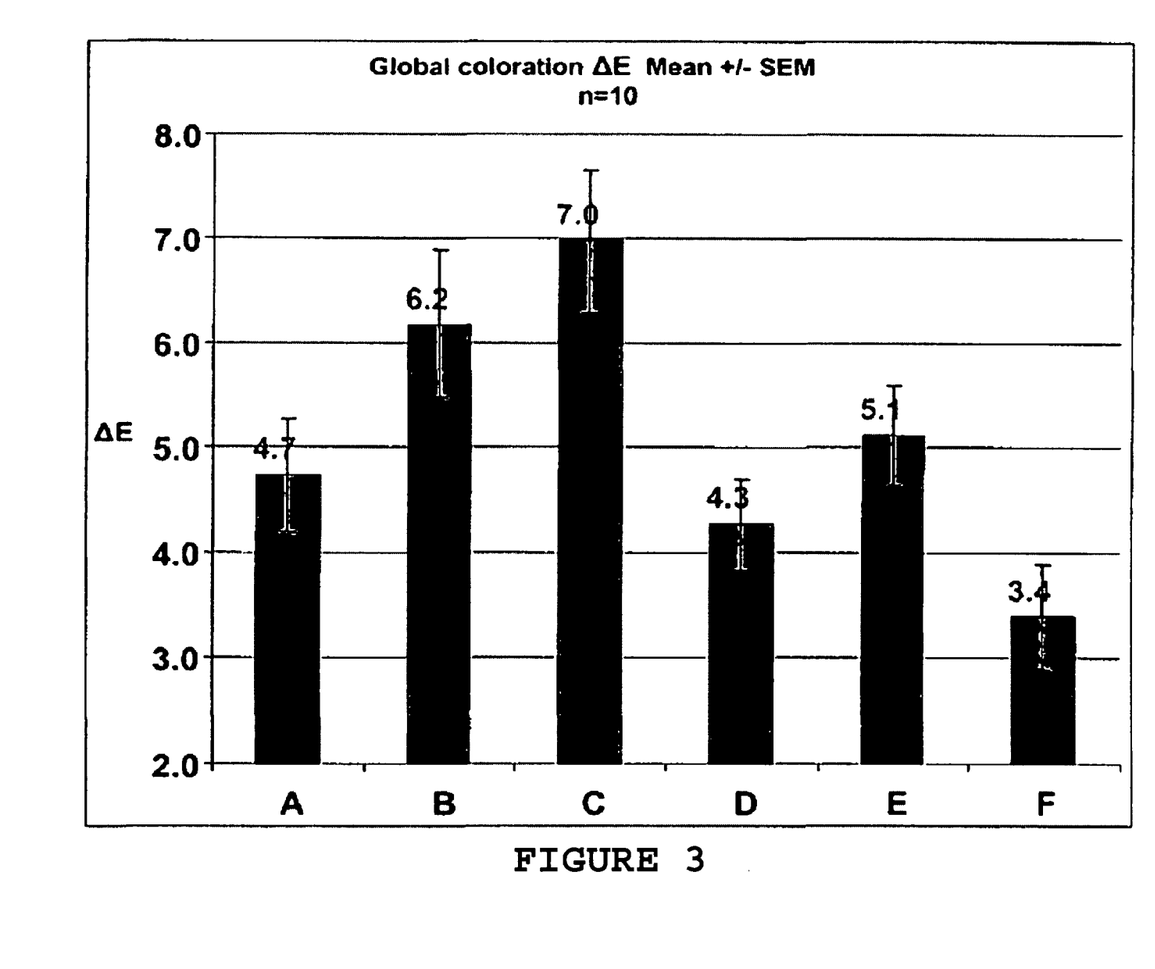
FIG. 3 shows the results of measurement of Persistent Pigment Darkening (PPD) for samples A-F.

Each sample was measured against sample C, which is the control formulation containing only the carrier and no active. Referring to FIG. 3, the following results were observed.

Sample A, containing 2% phloretin, significantly reduced the intensity of the UVA induced Persistent Pigment Darkening (PPD) (p=0.016).

Sample B, containing 15% vitamin C, did not show significant differences in the intensity of the UVA induced Persistent Pigment Darkening (PPD) vs. the control.

Sample D, containing 2% phloretin and 0.5% ferulic acid, significantly reduced the intensity of the UVA induced Persistent Pigment Darkening (PPD) (p=0.003).

Sample E, containing 15.3% Vitamin C, 0.5% ferulic acid and 1% Vitamin E significantly reduced the intensity of the UVA induced Persistent Pigment Darkening (PPD) (p=0.018).

Sample F, containing 2% phloretin, 0.5% ferulic acid and 15.3% vitamin C, significantly reduced the intensity of the UVA induced Persistent Pigment Darkening (PPD) (p=0.000).

In summary the results for Set 1 may be expressed as follows: Student's T-Test on pairs of data (n=10):

| Formula vs. control | Δa* | Visual | ΔE |
|---|---|---|---|
| A | ** | ** | ** |
| Phloretin: 2% | (p = 0.013) | (p = 0.018) | (p = 0.016) |
| B | NSD | ** | NSD |
| Vitamin C: 15% | | (p = 0.033) | |
| D | ** | ** | ** |
| Phloretin: 2% | (p = 0.007) | (p = 0.002) | (p = 0.003) |
| Ferulic Acid: 0.5% | | | |
| E | ** | ** | ** |
| Vitamin C: 15.3% | (p = 0.023) | (p = 0.004) | (p = 0.018) |
| Ferulic Acid: 0.5% | | | |
| Vitamin E: 1% | | | |
| F | ** | ** | ** |
| Vitamin C: 15.3% | (p = 0.001) | (p = 0.006) | (p = 0.000) |
| Ferulic Acid: 0.5% | | | |
| Phloretin: 2% | | | |

** Significant difference vs. control
* Trend
NSD: No Significant Difference

Set 2 Results

UVA Induced Erythema

Figure 4:
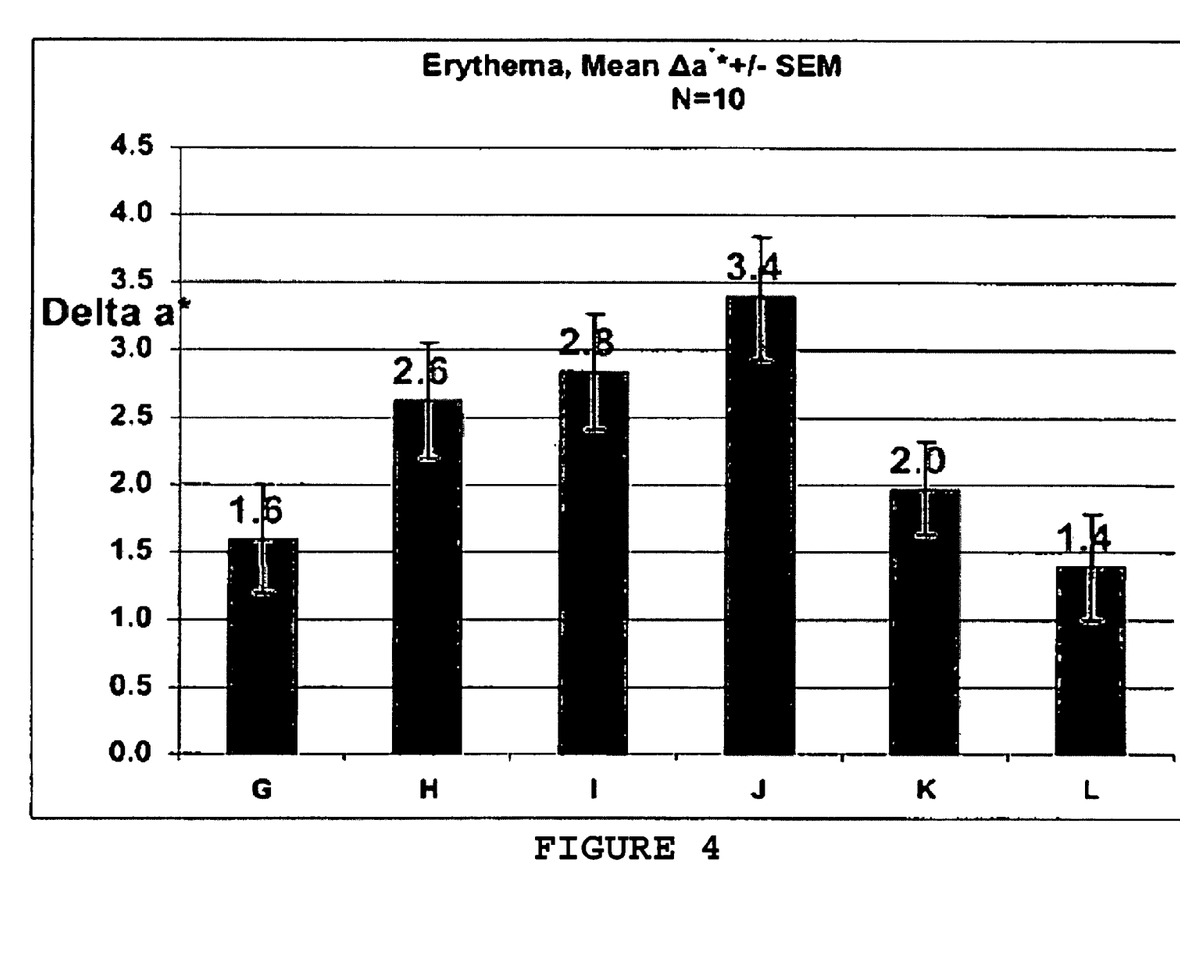
FIG. 4 shows the results of colormetric measurement of UVA induced erythema for samples G-L.

Each sample was measured against sample J, which is the control formulation containing only the carrier and no active. Referring to FIG. 4, the following results were observed.

Sample G, containing 15% Vitamin C, 0.5% Ferulic acid, 2% Phloretin and 0.02% Vitamin E, significantly reduced the intensity of the UVA induced erythema (p=0.012).

Sample H, containing 15% Vitamin C and 2% Phloretin, did not show any significant difference at the 95% confidence level.

Sample I, containing 0.5% Ferulic acid, did not show any significant difference at the 95% confidence level.

Sample K, containing 15.3% Vitamin C, 0.5% Ferulic Acid, and 1.0% Vitamin E, significantly reduced the intensity of the UVA induced erythema (p=0.018)

Sample L, containing 15% Vitamin C, 0.5% Ferulic acid and 2% Phloretin, significantly reduced the intensity of the UVA induced erythema (p=0.026).

Visual Assessment of UVA Induced Erythema

Figure 5:
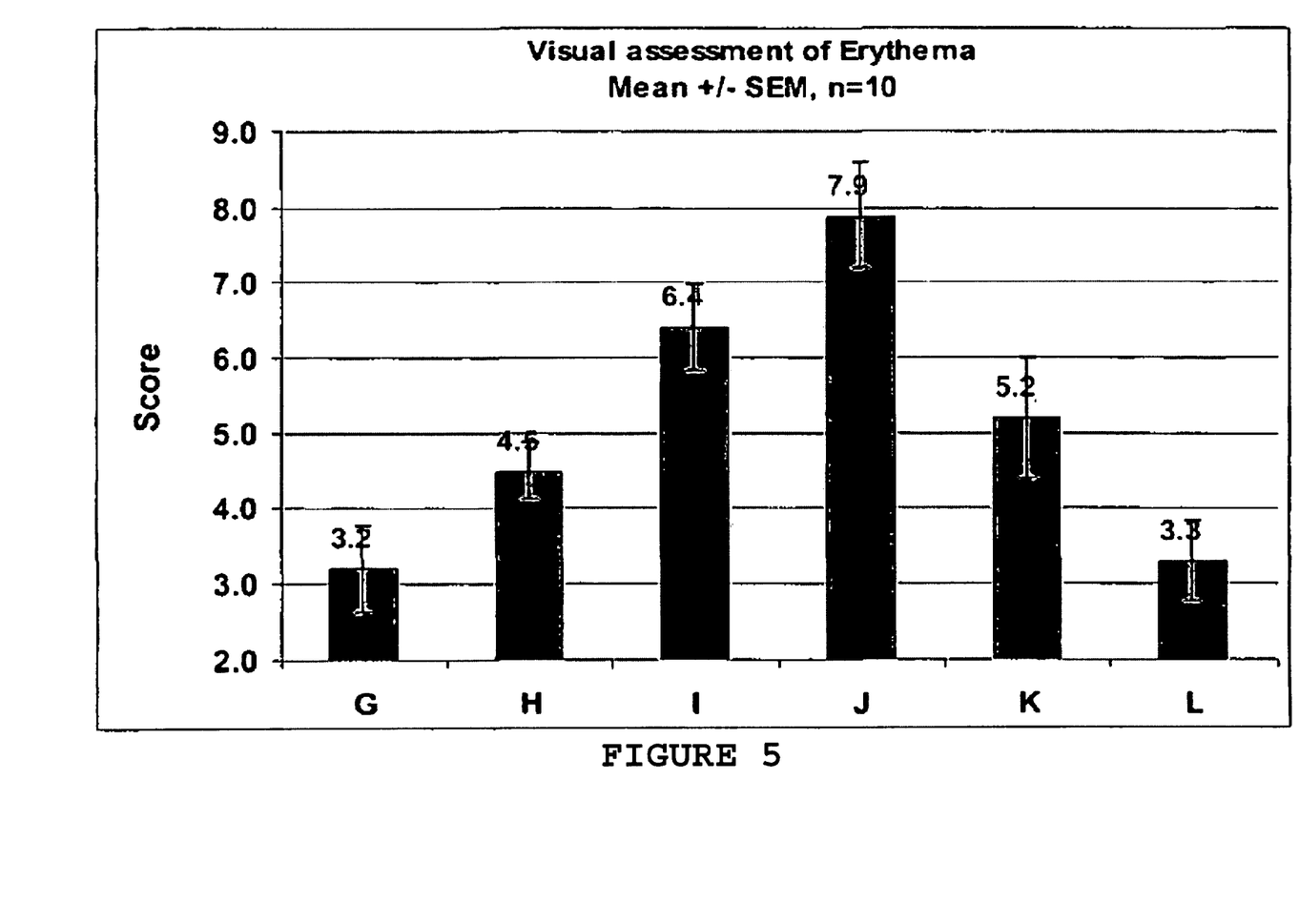
FIG. 5 shows the results of visual assessment of UVA induced erythema for samples G-L.

Each sample was measured against sample J, which is the control formulation containing only the carrier and no active. Referring to FIG. 5, the following results were observed.

Sample G, containing 15% Vitamin C, 0.5% Ferulic acid, 2% Phloretin and 0.02% Vitamin E, visually significantly reduced the intensity of the UVA induced erythema (p=0.016).

Sample H, containing 15% Vitamin C and 2% Phloretin, visually significantly reduced the intensity of the UVA induced erythema (p=0.006).

Sample I, containing 0.5% Ferulic acid, visually significantly reduced the intensity of the UVA induced erythema (p=0.011).

Sample K, containing 15.3% Vitamin C, 0.5% Ferulic Acid, and 1.0% Vitamin E, visually significantly reduced the intensity of the UVA induced erythema (p=0.007).

Sample L, containing 15% Vitamin C, 0.5% Ferulic acid and 2% Phloretin, visually significantly reduced the intensity of the UVA induced erythema (p=0.012).

Persistent Pigment Darkening (PPD)

Figure 6:
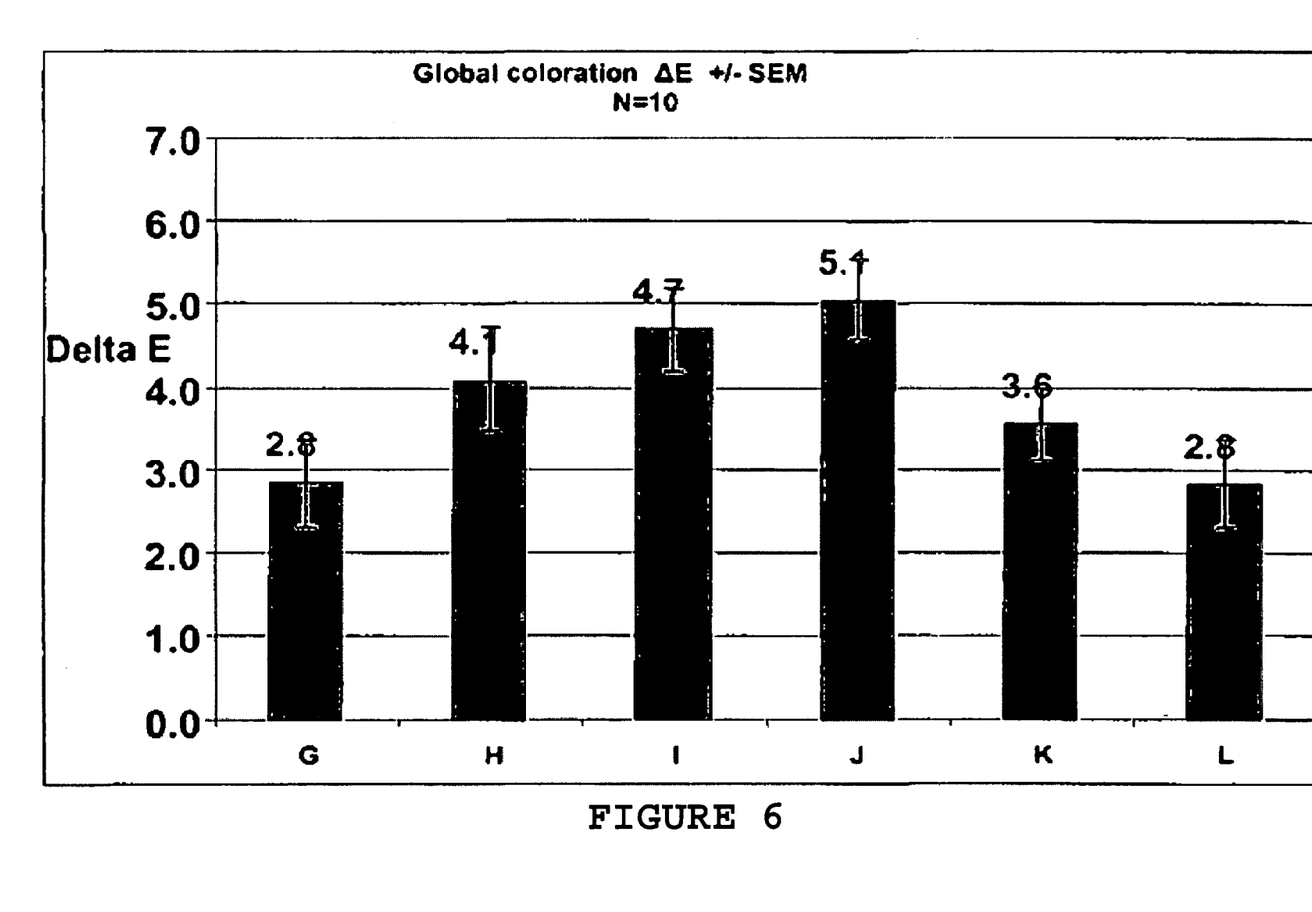
FIG. 6 shows the results of measurement of Persistent Pigment Darkening (PPD) for samples G-L.

Each sample was measured against sample J, which is the control formulation containing only the carrier and no active. Referring to FIG. 6, the following results were observed.

Sample G, containing 15% Vitamin C, 0.5% Ferulic acid, 2% Phloretin and 0.02% Vitamin E, significantly reduced the intensity of the UVA induced Persistent Pigment Darkening (PPD) (p=0.002).

Sample H, containing, 15% Vitamin C and 2% Phloretin, did not show any significant difference at the 95% confidence level.

Sample I, containing 0.5% Ferulic acid, did not show any significant difference at the 95% confidence level.

Sample K, containing 15.3% Vitamin C, 0.5% Ferulic Acid, and 1.0% Vitamin E, reduced the intensity of UVA induced Persistent Pigment Darkening (PPD) (p=0.055).

Sample L, containing 15% Vitamin C, 0.5% Ferulic acid and 2% Phloretin, significantly reduced the intensity of UVA induced Persistent Pigment Darkening (PPD) (p=0.027).

In summary the results for Set 2 may be expressed as follows:

Student's T-Test on pairs of data (n=10):

| Formula vs. control | Δa* | Visual | ΔE |
|---|---|---|---|
| G | ** | ** | ** |
| Vitamin C: 15% | (p = 0.012) | (p = 0.016) | (p = 0.002) |
| Ferulic Acid: 0.5 | | | |
| Phloretin: 2% | | | |
| Vitamin E: 0.02% | | | |
| H | NSD | ** | NSD |
| Vitamin C: 15% | | (p = 0.006) | |
| Phloretin: 2% | | | |
| I | NSD | ** | NSD |
| Ferulic Acid: 0.5% | | (p = 0.011) | |
| K | ** | ** | * |
| Vitamin C: 15.3% | (p = 0.018) | (p = 0.007) | (p = 0.055) |
| Ferulic Acid: 0.5% | | | |
| Vitamin E: 1% | | | |
| L | ** | ** | ** |

-continued

| Formula vs. control | Δa * | Visual | ΔE |
|---|---|---|---|
| Vitamin C: 15.3%<br>Ferulic Acid: 0.5%<br>Phloretin: 2% | (p = 0.026) | (p = 0.012) | (p = 0.027) |

** Significant difference vs. control
* Trend
NSD: No Significant Difference

What is claimed is:

1. A process for reducing radical-induced damage to skin for effects of radical-induced damage, comprising contacting the skin with a composition comprising:
    (a) phloretin in an amount of about 1% to about 2% by weight, based on the total weight of the composition;
    (b) ferulic acid in an amount of about 0.5% by weight, based on the total weight of the composition;
    (c) ascorbic acid in an amount of about 10% or about 15% by weight, based on the total weight of the composition;
    (d) at least one non-aqueous organic solvent comprising a monohydric alcohol selected from the group consisting of ethanol, isopropanol, hexyldecanol, benzyl alcohol, propyl alcohol, and isopropyl alcohol, and at least one dihydric alcohol selected from the group consisting of hexylene glycol, diethylene glycol, ethylene glycol, propylene glycol, 1,2-butylene glycol, 1,5-pentanediol, triethylene glycol, and dipropylene glycol;
    (e) water, as a co-solvent; and
    (f) optionally, vitamin E, in an amount of about 0.02% by weight, based on the total weight of the composition,
    wherein the composition does not contain a glycol ether, a monomeric ether, and a polymeric ether.

2. The process of claim 1, wherein the composition further comprises the vitamin E.

3. The process of claim 1, wherein the composition comprises about 1% by weight of phloretin.

4. The process of claim 1, wherein the composition comprises about 2% by weight of phloretin.

5. The process of claim 1, wherein the composition comprises about 5% by weight of ascorbic acid.

6. The process of claim 1, wherein the composition comprises about 10% by weight of ascorbic acid.

7. The process of claim 1, wherein the at least one non-aqueous solvent consists of ethanol, propylene glycol and pentylene glycol.

8. The process of claim 1, wherein the at least one non-aqueous solvent consists of ethanol, dipropylene glycol and butylene glycol.

9. The process of claim 1, wherein the composition further comprises a silicone surfactant.

* * * * *